Figure 1:
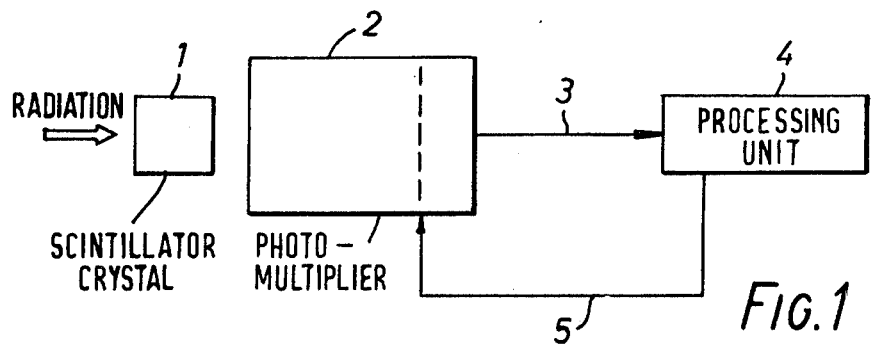

United States Patent [19]

Hounsfield

[11] 4,091,287

[45] * May 23, 1978

[54] SCANNING RADIOLOGY WITH INITIAL SCAN FOR ADJUSTING SYSTEM SO THAT DETECTOR MEANS OPERATES WITHIN ITS PREFERRED RANGE

[75] Inventor: Godfrey Newbold Hounsfield, Newark, England

[73] Assignee: EMI Limited, Hayes, England

[*] Notice: The portion of the term of this patent subsequent to May 11, 1993, has been disclaimed.

[21] Appl. No.: 653,114

[22] Filed: Jan. 28, 1976

Related U.S. Application Data

[62] Division of Ser. No. 572,740, Apr. 29, 1975, Pat. No. 3,956,633.

[30] Foreign Application Priority Data

May 8, 1974 United Kingdom .............. 20259/74

[51] Int. Cl.² .................. A61B 6/02; G01N 23/08
[52] U.S. Cl. .................... 250/362; 250/445 T
[58] Field of Search .............. 250/360, 362, 445 T, 250/363 S

[56] References Cited

U.S. PATENT DOCUMENTS 3,924,129  12/1975  Lemay .............................. 250/362
3,956,633   5/1976  Hounsfield ....................... 250/362

Primary Examiner—Alfred E. Smith
Assistant Examiner—T. N. Grigsby
Attorney, Agent, or Firm—Cooper, Dunham, Clark, Griffin & Moran

[57] ABSTRACT

In a radiological apparatus, arranged to produce a representation of the variation of absorption of penetrating radiation over a planar, cross-sectional slice of a body under examination, the radiation emergent from the body along a plurality of paths in the plane of the slice is detected by detector means including one or more photomultipliers. The output signals from the photomultiplier or photomultipliers are monitored and compared with upper and lower threshold levels which represent the extremes of substantially linear operation of the photomultiplier or photomultipliers. In the event of the output signals departing from the range defined by said threshold levels a correction signal is generated and utilized to tend to restore the output signals within said range.

5 Claims, 3 Drawing Figures

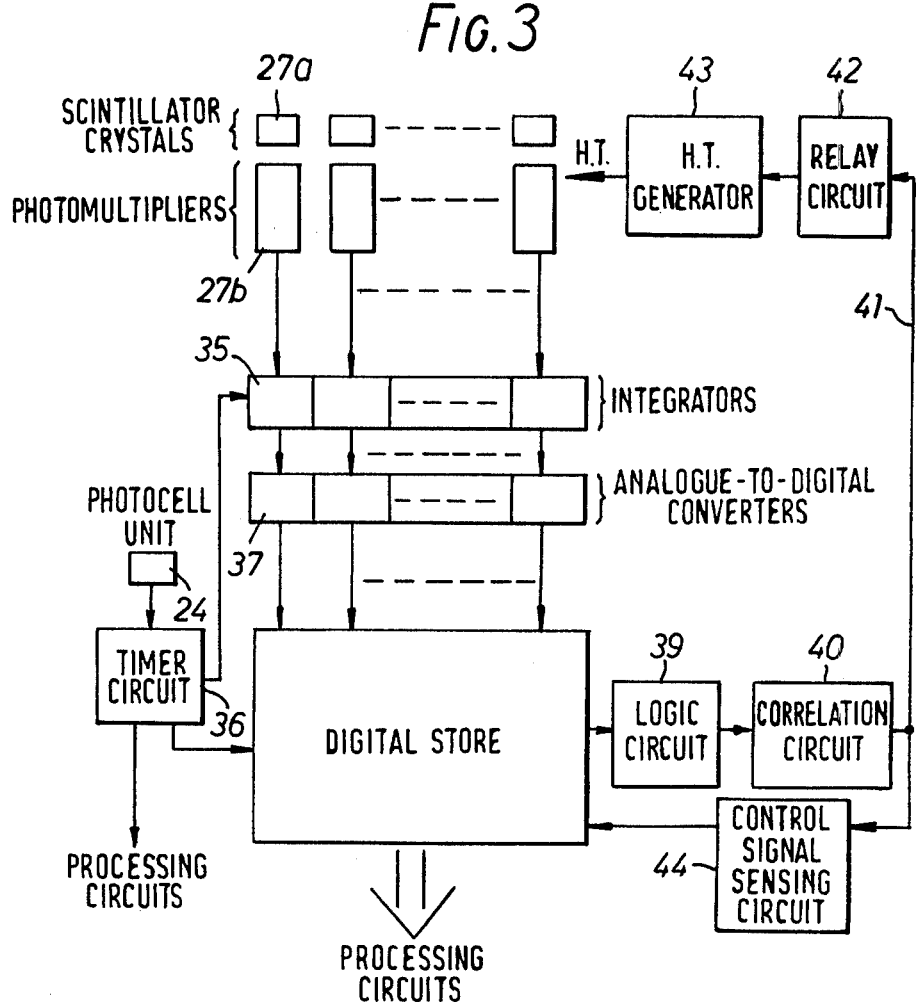

SCANNING RADIOLOGY WITH INITIAL SCAN FOR ADJUSTING SYSTEM SO THAT DETECTOR MEANS OPERATES WITHIN ITS PREFERRED RANGE

This is a divisional of application Ser. No. 572,740 filed Apr. 29, 1975, and now U.S. Pat. No. 3,956,633.

The present invention relates to radiology, and it relates especially to radiological apparatus of the kind in which penetrating radiation, such as X- or γ- radiation, is directed through a body along a plurality of paths disposed in a plane. The radiation emergent from the body is detected and used to determine the absorption suffered by the radiation on traversing each path, and the number of paths is arranged to be sufficient to permit the evaluation of the absorption (or transmission) coefficients of the elements of a two dimensional array of elements of the body, notionally delineated in said plane.

Typically, though not necessarily, the irradiation of the body is carried out in such a way that a source of a beam of the radiation and detector means are laterally traversed relative to the body, in said plane, so as to direct the radiation through the body along a set of said paths, and the source and detector means are then rotated through a small angle relative to the body about an axis perpendicular to the said plane so that a further lateral traverse can be executed to direct the radiation through the body along a further set of paths. The procedure of alternate rotational steps and lateral traverses is continued until the source and detector means have been rotated through a total angle at least approaching 180°.

The detector means conveniently comprises at least one combination of a scintillator device and a photomultiplier tube arranged to receive the light which is emitted by the scintillator device in response to the impingement of said radiation thereupon. Such photomultiplier tubes as are presently known exhibit a well defined characteristic curve relating the input light intensity to the output electrical signal. Said characteristic includes a substantially linear portion over a range of input light intensities but becomes non-linear for intensities above and below this range.

The evaluation of said coefficients is carried out by processing the output signals derived from said at least one photomultiplier, for example in the manner described in U.S. Pat. Ser. No. 3,778,614 or in the manner described in U.S. Pat. No. 3,924,129, and in order that the processing may be rendered as simple as possible whilst permitting the evaluation to be effected with a high degree of accuracy, it is desirable that the said at least one photomultiplier be constrained to operate within the linear region of its characteristic.

The aforementioned processing is carried out by means of a digital computer and this computer is supplied with all the output signals derived from said at least one photomultiplier.

In accordance with this invention, there is provided radiological apparatus for examining a body by means of penetrating radiation, such as X- or γ- radiation, including a source of said radiation supported so as to project said radiation through a cross-sectional slice of said body, detector means for detecting the radiation after it has traversed the slice of the body along at least one substantially linear beam path, and for producing electrical output signals indicative of the radiation detected thereby, scanning means for scanning said source and said detector means relative to said body, causing the source to sequentially project said radiation through said slice from a plurality of different locations and said detector means to detect the radiation emergent from the body along at least one substantially linear beam path for each of said locations and to produce corresponding electrical output signals, said scanning including at least an angular movement of said source and said detector means around the body about an axis intersecting said slice; the beam paths irradiated as a consequence of the scanning including a plurality of sets of paths, each set being disposed at a respective angle, or mean angle, in the slice with respect to the body and each set including paths distributed over a substantial part of said slice, wherein the detector means exhibits a response characteristic which causes said output signals to vary in a predetermined manner in response to different amounts of radiation received thereby, said received amounts being dependent, in each case, on the absorption suffered by the radiation on traversing the body along the respective path, and wherein the electrical output signals for an initially scanned set of said paths are used to set the relationship between the output signals for subsequently scanned sets and the absorptions suffered by the radiation on traversing the body along the respective beam paths in said subsequently scanned sets to a level at which said detector means tends to operate consistently within a restricted part of said response characteristic; evaluating means being provided for processing the output signals relating to said subsequently scanned sets to produce a representation of the variation of absorption of said radiation with position over said slice.

Figure 2:
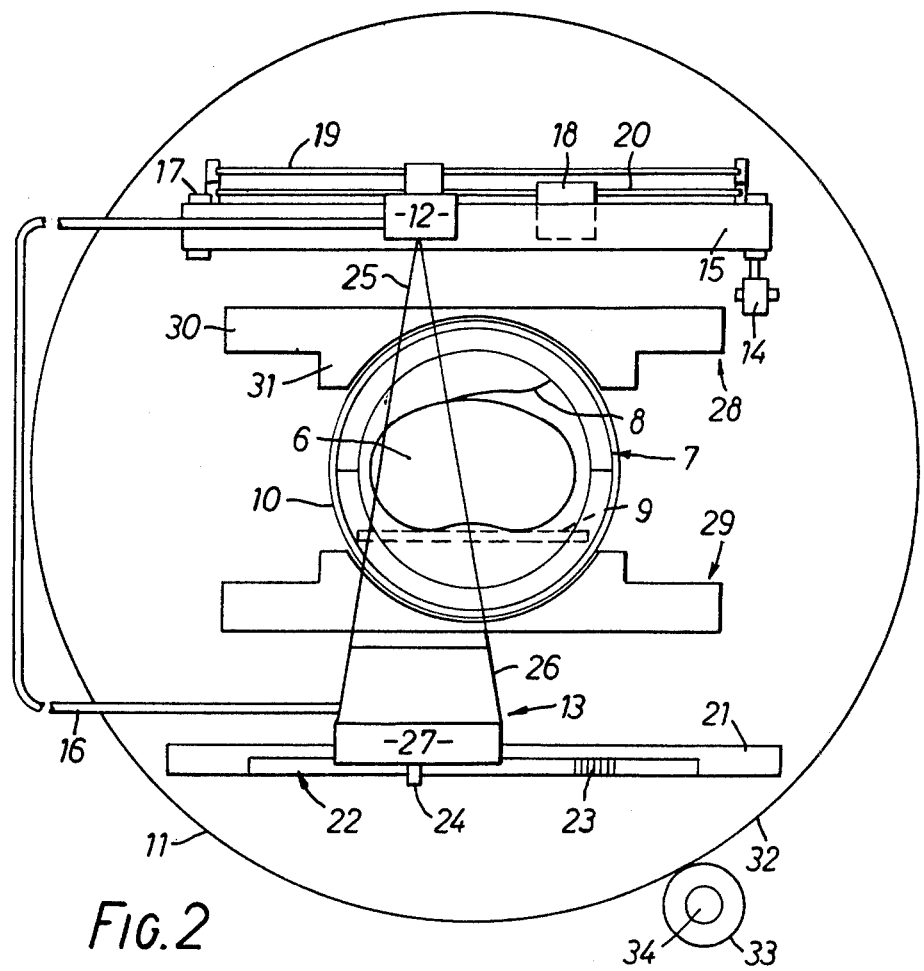

In order that the invention may be clearly understood and readily carried into effect, one embodiment thereof will now be described, by way of example only, with reference to the accompanying drawing, of which:

FIG. 1 shows, in simplified and block diagrammatic form, part of an apparatus in accordance with one example of the invention, FIG. 2 shows, in more detail and in end elevation, apparatus which incorporates another example of the invention, and FIG. 3 shows, in block diagrammatic form, a circuit arrangement for use with the apparatus of FIG. 2.

Referring now to FIG. 1, penetrating radiation from a source (not shown) emerges from a body (not shown) and impinges upon a scintillator crystal 1 of known kind. The light emitted by the crystal 1 falls upon a photomultiplier tube 2 which provides electrical output signals along a line 3 to a processing unit 4 which may comprise a digital computer.

In this example of the invention, a single scintillator/photomultiplier combination is used and the source and the detector are scanned relative to the body in a combination of lateral traverses and rotational steps as described hereinbefore. During each lateral traverse, the tube 2 provides, successively, output signals indicative of the absorption suffered by said radiation on traversing a plurality of closely adjacent, parallel paths through the body.

The processing unit 4, which receives these output signals, is also arranged to provide control signals on a line 5 if the output signal relating to any one or more of the paths irradiated during a linear traverse is indicative of a light intensity outside the aforementioned linear range of the photomultiplier characteristic being incident upon the tube 2.

The control signals on line 5 are applied to the photomultiplier tube 2 prior to the next linear traverse in such a way as to control its gain, for example by varying the operation of H.T. voltage applied thereto or, as shown in FIG. 1, by application to any suitable control electrode of the tube. In either event, the gain of the photomultiplier is changed by an extent dependent upon the amount by which said light intensity falls outside said range, thus tending to ensure that the tube 2 operates on the linear part of its characteristic for the next linear traverse. Of course, instead of utilising the control signals to control the gain of the tube over the whole of the next linear traverse, the control could be applied solely to paths adjacent the path or paths which gave rise to the output signals responsible for the generation of said control signals.

It will be appreciated that since the gain control is effected under the control of the processing unit 4, the unit is capable of allowing for the changes of gain when the computation is carried out.

Although the invention has been described in relation to an example in which only a single crystal/photomultiplier combination is used, it will be evident to those skilled in the art that the invention is also applicable to apparatus including multiple combinations of scintillators and photomultipliers and such an arrangement will now be described with reference to FIGS. 2 and 3.

When multiple scintillator/photomultiplier combinations are used, the processing unit can be arranged to produce a common control signal which is applied to all said combinations or an individual control signal for each combination, but in the example now to be described the former technique is used because of its greater practical simplicity.

Referring now to FIG. 2, a body 6 to be examined is disposed supine in the apparatus with the plane of interest arranged to coincide with the plane of the investigating radiation. The body is surrounded, in that plane, by a two-part collar 7, and trapped between the inside of the collar and the body 6 is an elongated bag 8 containing water or some other material which absorbs radiation to an extent similar to the tissue of body 6. The body, together with the bag 8 and the collar 7, remains stationary during the investigation, the body 6 being supported on a two-part bed, one part of which is indicated at 9. The other part of the bed cannot be seen in FIG. 2 because it extends outwardly from the plane of the drawing and has been omitted for clarity. The lower part of the collar 7 is rigidly secured to a stationary part of the apparatus, and the upper part thereof is clipped to the lower part once the body is correctly positioned for the examination.

The body is located in a circular aperture 10 in a turntable 11 which supports the components now to be described and enables them to orbit around the body, about an axis which extends perpendicularly to the plane of the drawing and passes through the centre of the aforementioned aperture. The turntable 11 carries an X-ray source 12 and an associated detector assembly 13, which are disposed on opposite sides of the aperture 10, and the components 12 and 13 are enabled to reciprocate relative to the body 6 by virtue of an electrical motor 14 which drives an endless toothed belt 15, to which the X-ray source 12 is mounted. Detector assembly 13 is linked to the source 12 by means of a lightweight but rigid yoke 16 so that the detector assembly moves with the source. The belt 15 passes over an idler pulley 17 and also carries a counter-balance weight 18 which is arranged to travel in the opposite direction to the source and detector assembly, for the purpose of compensating out of balance forces due to the motion of the source and detector assembly. The source 12 and the weight 18 travel on respective linear bearings, which include rods 19 and 20 respectively, so that the belt 15 does not bear the weight of these massive members. Detector assembly 13, on the other hand, runs on a bearing which comprises a plate member 21 secured to the turntable 11; the assembly 13 being provided with suitable roller members (not shown) to run on the flat surface of the member 21, thus being arranged to limit fore-and-aft movement of the assembly 13.

Member 21 is also formed with a graticule 22 comprising a translucent region bearing opaque markings, as shown at 23, throughout its length. The detector assembly 13 carries with it as it moves a photocell detector unit 24 which is arranged to respond to the graticule 22 to provide electrical timing pulses, for use in controlling the operation of the processing, as will be more fully described hereinafter.

The source 12 is arranged to produce a planar, fan-shaped beam 25 of X-radiation which is split into a plurality of finger-like beams of small cross-section by a bank of collimators 26 which forms part of the detector assembly 13. In this example, the collimators 26 are arranged to split the beam 25 into thirty finger-like beams, and correspondingly the detector assembly includes thirty detectors. Each detector, in this example, comprises the combination of a scintillator crystal and a photomultiplier tube, these components being indicated by the general reference 27 in FIG. 2, but being shown as separate entities 27a and 27b respectively in FIG. 3. The angle of the beam 35 is, in this example, ten degrees.

On either side of the aperture 10 there is provided a compensating member 28, 29 formed, for example, of aluminium. These members are disposed, one between the source and the body and the other between the body and the detector assembly, so as to rotate with the turntable 11, but they do not reciprocate with the yoke 16 and its attachments. They are provided to tend to equalise the absorption suffered by radiation from the source 10 as it traverses different paths through the body, thus limiting the dynamic range of radiation levels impinging on the crystals 27a and thereby the dynamic range of light levels to be handled by the photomultipliers 27b. The members 28 and 29 also include peripheral portions such as 30 and 31; the portions 30 being arranged to simulate a region of reference intensity — for example a path of known length through water. The portions 31 on the other hand are caused to be highly absorbent to the radiation so as to provide a zero or 'black level' reference signal and can, for example, carry a portion of lead or some other highly absorbent material. The output signals obtained when the regions 30 and 31 are disposed between the source and the detector assembly are used to normalise the readings obtained when the body is irradiated.

Turntable member 10 is formed with gear teeth at 32 around its periphery and it is driven, via a driving gear 33, by means of a motor 34, and the scanning operation comprises alternate linear traverses and rotational steps as follows. First the motor 14 is energised to sweep the source 12 and detector assembly 13 linearly across the turntable 11, thus causing these components to execute a linear scan relative to the body 6. This single linear scan having been carried out, the motor 34 is then energised to cause the turntable 11, and thus all the components mounted thereon, to rotate around the body through an angle corresponding to the angle of the fan beam 25 — i.e. through 10° in this examle. A second linear scan of the source and detector assembly is then achieved by causing motor 14 to drive belt 15 in the opposite direction to that in which it was driven during the first traverse. The sequence of alternate linear traverses and rotational steps is carried on until the body 6 has been irradiated from the desired number of different directions. In this connection it will be observed that the rotational steps are carried out during periods of reversal of the linear scanning motion. It can be advantageous for the rods 19 and 20 to carry, at their ends, resilient buffer members arranged to absorb the energy of impact of the source 12 or the weight 18 as the case may be and to use such absorbed energy to assist in the reversal of the linear motion. By this means, strains upon the belt 15 and the motor 14 can be reduced.

Turning now to FIG. 3, there is shown, in block diagrammatic form, a circuit arrangement for handling the electrical signals provided by the photomultipliers 27b, under control of the timing pulses produced by unit 24, in accordance with the principles of this invention.

Each of the thirty photomultipliers 27b feeds a respective integrator circuit, the respective circuits being shown in a block 35, and the integration times of all the integrators are determined by timing pulses, derived from a timing control circuit 36 which receives the pulses provided by the aforementioned photocell unit 24. Each integrator in the block 35 feeds a respective analogue-to-digital converter, the converters being shown in a block 37, and thence a digital store 38.

A logic circuit 39 is connected to the store 38 and is arranged to receive therefrom all the signals derived during each linear scan executed by the source 12 and detector assembly 13 relative to the body 6. The logic circuit 39 is arranged to compare all of the signals relating to a linear scan so as to determine the highest and lowest amplitude signals in the whole series, and it is also arranged to note the reference readings obtained when the parts 30 of the members 28 and 29 are irradiated.

The readings selected by the logic curcuit 39, for example by successive comparisons of the signals in pairs, thus indicate the highest and lowest signals provided by any detector during a linear scan, as well as a reference reading. These readings are correlated, in a correlation circuit 40, with stored values indicative of the maximum and minimum signals which it is permissible to derive from the photomultipliers whilst operating them as the aforementioned linear part of their characteristics. Such values are stored in the form of look-up tables, in known manner. If the result of the correlation is that the photomultipliers are, or are in danger of, being operated outside said linear region, the circuit 40 generates a control signal to rectify the situation prior to the next linear scan. This signal is applied via a line 41 and a circuit 42, which will be referred to hereinafter, to an H.T. generator 43 of commercially available kind, which supplies all the photomultiplier tubes 27b with their operational H.T. voltage. The control signal on line 41 is arranged to cause the generator 43 to alter the H.T. applied to the photomultipliers in a sense tending to preset the gains of the photomultipliers for the next linear scan, ensuring as far as possible that all of the photomultipliers are operated on the linear range of their characteristics.

This can be done, for example, by means of the circuit 42, which contains relay operable switch contacts arranged to respond to the control signals from circuit 40 to switch appropriate resistances into or out of the circuits of the generator 43.

It is, of course, essential for the processing circuits, which will correlate the stored signals to evaluate the absorption of elements of the body, to compensate for changes of photomultiplier gain, and thus the line 41 is also coupled to a circuit 44 which senses the control signals from circuit 40 and relays information relating to the magnitude thereof to the store 38. These signals are stored in association with the digital signals applied to store 38 from the bank of converters 37 and are used during the subsequent processing of the stored signals to allow for the aforementioned change of gain. Store 38, together with circuits 39 and 40, constitutes part of a digital computer which is arranged to effect the processing in such a way that the absorption coefficients of a two-dimensional, notional matrix of elements defined in the plane of interest in the body 6, are calculated to a high degree of accuracy. The computer is connected to any suitable display means (not shown) to produce a representation of the calculated absorption values.

It will be evident that the store 38 is responsive to timing signals from the circuit 36 so that the respective digital signals can be identifiably stored in respective locations thereof, and so that any signals applied to store 38 by circuit 44 can be associated with the correct stored values. This is done in order that the stored values can be properly normalised, to allow for the effects of changing the gain of the photomultipliers, by adjusting their amplitude accordingly. For example if, during linear scan $n$ the photomultiplier gains were set to a value $x$, whereas for linear scan $(n+1)$ the gains are set to a different value $y$, then it is necessary for the readings obtained during scan $(n+1)$ to be multiplied by a factor $(x/y)$ to render the two sets of readings compatible.

In a preferred method of operating an apparatus in accordance with the embodiment just described, an initial traverse of the source 12 and detector assembly 13 relative to the body 6 is carried out, not for the purpose of obtaining output signals indicative of radiation absorption but for the purpose of setting the photomultiplier gains at an appropriate level for the commencement of the scanning sequence proper. For this initial traverse, the photomultiplier gains are set at a low level so that the minimum absorption likely to be encountered (corresponding to the highest amplitude of output signal) will not overload any of the photomultipliers. The circuits 39 and 40 are arranged to provide the appropriate control signal to increase the gains of the photomultipliers to a level at which all signals likely to be encountered on the next linear scan (the first scan as regards the provision of output signals indicative of absorption) will fall within the linear range of the photomultiplier characteristics.

Clearly the circuits 39 and 40 continue to monitor the signal levels stored in store 38 throughout the examination period, and provide control signals to the circuit 42, and thus control the level of the H.T. produced by generator 43, as appropriate. The computer is supplied with information concerning these control signals via circuit 44 and store 38 so as to enable the aforementioned normalisation to be carried out. It is preferable for the circuits 39 and 40 to be arranged so that control signals are only generated in response to variations in signal amplitude which exceed a predetermined threshold level, so that the H.T. generator is not continuously subjected to minor variations, but is only changed in response to variations which exceed said threshold level. Circuit 40 can be interconnected with circuit 43 by means of a plurality of cables, each of which can operate a respective relay contact in circuit 42. In this case the arrangement can be made such that as the correlation circuit 40 provides an output signal on one or more of the cables in dependence upon the H.T. required to set the gains of the photomultipliers at the appropriate level.

The kind of scanning described in the examples set out above is illustrative only. For example the source of radiation may be arranged to produce a sectoral-shaped swath of radiation which is wide enough to embrace the body. In this case a plurality of scintillator/photomultiplier combinations are distributed across the width of the swath and no linear traverse is necessary since the scanning can then be achieved by rotation only.

What I claim is:

1. Radiological apparatus including a radiation source for projecting radiation through a body, detector means for detecting radiation transmitted from said source at least one beam path through the body and for producing a respective output signal for each such beam path, said detector means having a predetermined, preferred range of operation, scanning means for scanning said source and said detector means relative to the body to cause said detector means to produce a plurality of output signals relating to sets of co-planar beam paths at different angles, each set including beam paths distributed over a substantial area of the body in the plane of said paths, and calibrating means for deriving, during an initial scanning movement, calibration signals relating to a calibrating set of beam paths distributed across said substantial area and for adjusting the relationship between the calibration signals and the absorption suffered by the radiation on traversing the body along the respective beam paths such that, during subsequent scanning movements, the detector means operates substantially within said preferred range, and evaluating means for utilising the output signals produced during said subsequent scanning movements to evaluate the absorption of said radiation by elements of said area of the body.

2. Apparatus according to claim 1 including means for conveying signals indicative of the adjustment applied to said calibration signals to said evaluating means to allow said adjustment to be accounted for in the evaluation.

3. Apparatus according to claim 1 wherein said scanning means causes said source and said detector means to perform alternate lateral and rotational scanning movements relative to the body, the detector means being arranged to produce, for each lateral scanning movement, output signals relating to a respective set of beam paths, and wherein the calibration signals are produced during an initial lateral scanning movement.

4. Apparatus according to claim 1 wherein the said relationship which is adjusted is that between the radiation incident upon said detector means and the corresponding calibration signal.

5. Apparatus for examining a body by means of penetrating radiation, such as X- or γ- radiation, including a source of said radiation supported so as to project said radiation through a cross-sectional slice of said body, detector means for detecting the radiation after it has traversed the slice of the body along at least one substantially linear beam path, and for producing electrical output signals indicative of the radiation detected thereby, scanning means for scanning said source and said detector means relative to said body, causing the source to sequentially project said radiation through said slice from a plurality of different locations and said detector means to detect the radiation emergent from the body along at least one substantially linear beam path for each of said locations. and to produce corresponding electrical output signals, said scanning including at least an angular movement of said source and said detector means around the body about an axis intersecting said slice; the beam paths irradiated as a consequence of the scanning including a plurality of sets of paths, each set being disposed at a respective angle, or mean angle, in the slice with respect to the body and each set including paths distributed over a substantial part of said slice, wherein the detector means exhibits a response characteristic which causes said output signals to vary in a predetermined manner in response to different amounts of radiation received thereby, said received amounts being dependent, in each case, on the absorption suffered by the radiation on traversing the body along the respective path, and wherein the electrical output signals for an initially scanned set of said paths are used to set the relationship between the output signals for subsequently scanned sets and the absorptions suffered by the radiations on traversing the body along the respective beam paths in said subsequently scanned sets to a level at which said detector means tends to operate consistently within a restricted part of said responsive characteristic; evaluating means being provided for processing the output signals relating to said subsequently scanned sets to produce a representation of the variation of absorption of said radiation with position over said slice.

* * * * *

UNITED STATES PATENT AND TRADEMARK OFFICE
CERTIFICATE OF CORRECTION

PATENT NO. : 4,091,287
DATED : May 23, 1978
INVENTOR(S) : GODFREY NEWBOLD HOUNSFIELD

It is certified that error appears in the above-identified patent and that said Letters Patent are hereby corrected as shown below:

Claim 1 (Column 7, line 26) after "source" insert -- along --.

Claim 5 (Column 8, line 50) delete "responsive" and insert -- response --.

Signed and Sealed this

Fifteenth Day of May 1979

[SEAL]

Attest:

RUTH C. MASON
*Attesting Officer*

DONALD W. BANNER
*Commissioner of Patents and Trademarks*